United States Patent [19]
Okamura et al.

[11] Patent Number: 5,866,574
[45] Date of Patent: Feb. 2, 1999

[54] PANCREATITIS REMEDY

[75] Inventors: Yuko Okamura; Junichi Shimada; Toru Noji; Chikako Katagiri; Akira Karasawa, all of Sunto-gun, Japan

[73] Assignee: Kyowa Hakko Kogyo Co., Ltd., Tokyo, Japan

[21] Appl. No.: 56,710

[22] Filed: Apr. 8, 1998

[30] Foreign Application Priority Data

Apr. 10, 1997 [JP] Japan ..................................... 9-091960

[51] Int. Cl.$^6$ ........................ A61K 31/53; A61K 31/495; A61K 31/505
[52] U.S. Cl. .......................... 514/245; 514/248; 514/255; 514/259
[58] Field of Search .................... 514/245, 248, 514/259, 255

[56] References Cited

U.S. PATENT DOCUMENTS 3,267,104  8/1966  Hermans et al. ...................... 260/268
4,766,125  8/1988  Van Daele ............................ 514/255
5,605,900  2/1997  Fujiwara et al. ...................... 514/245

FOREIGN PATENT DOCUMENTS 0285219  10/1988  European Pat. Off. .
0582164   2/1994  European Pat. Off. .

OTHER PUBLICATIONS

IJzerman et al., "Inhibition of nucleoside transport by a new series of compounds related to Iidoflazine and mioflazine" Eur. Journal of Pharmacology, No. 172 (1989) pp. 273–281.

Nomoto et al., "Studies on Cardiotonic Agents. I. Synthesis of Some Quinazoline Derivatives" Chem. Pharm. Bull., No. 38(6) (1990) pp. 1591–1595.

*Primary Examiner*—Raymond Henley, III
*Attorney, Agent, or Firm*—Fitzpatrick, Cella, Harper & Scinto

[57] ABSTRACT

The present invention relates to a prophylactic agent or a therapeutic agent of pancreatitis, containing an adenosine uptake inhibitor or a pharmaceutically acceptable salt thereof.

3 Claims, 2 Drawing Sheets

PANCREATITIS REMEDY

FIELD OF THE INVENTION

The present invention relates to a prophylactic agent of pancreatitis or a therapeutic agent thereof.

BACKGROUND OF THE INVENTION

Pancreatitis is a disease of which the onset is triggered by activation of pancreatic enzymes in pancreas, so that pancreas is auto-digested by activated pancreatic enzymes. As therapeutic agents of pancreatitis, use is made of for example gastric acid secretion suppressing agents, proteinase inhibiting agents, analgesics and anti-spasmodics, antibiotics and the like (Practice of Gastro-Intestinal Diagnostics 6, edited by Tadahiko Kozu, chief editor, Bunkodo, Tokyo, 1993).

More specifically, histamine $H_2$ receptor antagonists (blockers) including cimetidine, ranitidine, famotidine and the like are used as gastric acid secretion suppressing agents (Therapeutic Medicine Guide, '96 edition, edited by Medical Practice Editorial Committee, Bunkodo, Tokyo, 1996). Proteinase inhibiting agents include high-molecular urinastatin extracted from human urine and gabexate mesilate and nafamostat mesilate as lower molecular synthetic products [Mebio, 13(6), 74–80 (1996)]. As the analgesics and anti-spasmodics, use is made of non-steroidal, anti-inflammatory analgesics (indomethacin) and non-opioid analgesics (pentazocine). As the antibiotics, use is made of penicillin-series antibiotics with wide spectrum (piperacillin), and cefem-series antibiotics of first and second generations (cefazolin and cefmetazole) (Practice of Gastro-Intestinal Diagnostics 6, edited by Tadahiko Kozu, chief editor, Bunkodo, 1993). However, the pharmacological effects of any of these pharmaceutical agents are not sufficient. Thus, more excellent prophylactic or therapeutic agents of pancreatitis have been needed.

Adenosine causes various physiological effect through receptor ($A_1$, $A_{2A}$, $A_{2B}$, $A_3$) which present on plasma membrane. Adenosine uptake inhibitor maintains adenosine concentration around adenosine receptor and increase adenosine effect by inhibiting adenosine uptake into tissue.

Most of quinazoline derivatives represented by the following formula (I) to be used in accordance with the present invention have been known, and it has been known also that such derivatives have an adenosine uptake inhibitory activity and are effective for myocardial protection and prophylaxis or treatment of inflammation such as paw edema (WO94/19342, WO96/06841). Additionally, Chemical Pharmaceutical Bulletin, 38, 1591–1595 (1990) describes a 1,2,3,4-tetrahydro-2,4-dioxoquinazoline derivative with 1-(6,7-dimethoxy-4-quinazolyl)-4-piperidinyl group at position 3 and hydrogen, chloride atom or nitro group at position 6.

It has also been known that an N-aryl piperazine alkaneamide derivative with some relation to the compound represented by the following Formula (II) has various pharmacological actions. More specifically, Japanese Published Examined Patent Application No.232/69 describes that the derivative has coronary vasodilator action, central stimulant action, local anesthetic action, or anti-carrageenan action; Japanese Published Unexamined Patent Application No. 4774/83 describes that the derivative has an action of myocardial protection; Japanese Published Unexamined Patent Application No. 290869/88 describes that the derivative has an action of ameliorating sleep quality; and European Journal of Pharmacology, 172, 273–281 (1989) describes that the derivative has an action of inhibiting adenosine uptake. Furthermore, Japanese Published Unexamined Patent Application No. 157472/94 describes that N-piperazine acetamide derivatives of 4,5-diphenyloxazol, thiazole and imidazole have an action of inhibiting adenosine uptake and a neuroprotective action. Still additionally, Nucleosides & Nucleotides, 10, 975–982 (1991) describes that dipyridamole, dilazep, hexobendine, lidoflazine and R75231 have an action of inhibiting adenosine uptake.

However, it has not yet been known that the compound represented by Formula (I) or Formula (II) is effective for the prophylaxis or treatment of pancreatitis. No report has been published yet, indicating that a compound with an action of inhibiting adenosine uptake is effective for the prophylaxis or treatment of pancreatitis.

SUMMARY OF THE INVENTION

The object of the present invention is to provide an excellent prophylactic or therapeutic agent of pancreatitis.

The present invention relates to a prophylactic or therapeutic agent of pancreatitis, containing an adenosine uptake inhibitor or a pharmacologically acceptable salt thereof as the effective ingredient.

DETAILED DESCRIPTION OF THE INVENTION

The present inventors have found a novel finding that the adenosine uptake inhibitor or a pharmacologically acceptable salt thereof is widely effective for the prophylaxis or treatment of pancreatitis. In accordance with the present invention, the term "adenosine uptake inhibitor" means any of all compounds with an action of inhibiting adenosine uptake as one of the properties, irrespective of the structure or whether or not the agent is novel or known.

The examples include a quinazoline derivative represented by the following Formula (I);

wherein $R^1$ represents hydrogen, substituted or unsubstituted lower alkyl, alkenyl, or substituted or unsubstituted aralkyl; $R^2$, $R^3$, $R^4$ and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; $R^6$, $R^7$, $R^8$ and $R^9$ independently represent hydrogen, lower alkyl, hydroxy, substituted or unsubstituted lower alkoxy or aralkyloxy, or any adjoining two of them are combined to form methylenedioxy, or ethylenedioxy; $R^{10}$ represents hydrogen, substituted or unsubstituted lower alkyl, halogen, or $NR^{12}R^{13}$ (wherein $R^{12}$ and $R^{13}$ independently represent hydrogen, substituted or unsubstituted lower alkyl, cycloalkyl, substituted or unsubstituted aryl, or substituted or unsubstituted aralkyl; or $R^{12}$ and $R^{13}$ are combined together with N to form a substituted or unsubstituted heterocyclic group); $R^{11}$ represents hydrogen, lower alkyl, or halogen; and n represents 0, 1, or 2(WO94/19342 or WO96/06841); or a pharmacologically acceptable salt thereof, and a compound represented by the Formula (II);

wherein $R^{14}$ represents hydrogen, or lower alkyl; $R^{15}$ represents hydrogen, carbamoyl, mono- or di(lower alkyl) aminocarbonyl, lower alkoxycarbonyl, or carboxy; $R^{16}$ represents hydrogen, or lower alkyl; Ar represents substituted or unsubstituted aryl, or substituted or unsubstituted heterocyclic group; m represents 1, or 2; p represents an integer of 0 to 5; Q represents substituents selected from the group consisting of (a) to (m) represented by the following formulas;

wherein Y represents S, O, or NH; $Ar^1$ and $Ar^2$ independently represent substituted or unsubstituted aryl, or substituted or unsubstituted heterocyclic group [Japanese Published Examined Patent Application No. 232/69; Japanese Published Unexamined Patent Application No. 4774/83; European Journal of Pharmacology, 172, 273–281 (1989); or Japanese Published Unexamined Patent Application No.290869/88] or a pharmaceutically acceptable salt thereof, N-piperazineacetamide derivatives of 4,5-diphenyloxazol, thiazole and imidazole (Japanese Published Unexamined Patent Application No. 157472/94), dipyridamole, diazep, hexobenzine, lidofrazine, and R75231 [Nucleosides & Nucleotides, 10, 975–982 (1991)]. Preferable examples of the adenosine enhancing agent of the present invention include the compound represented by Formula (I) or Formula (II) or a pharmacologically acceptable salt thereof.

The compounds represented by Formula (I) are referred to as Compound (I) and the compounds represented by Formula (II) is referred to as Compound (II),hereinafter.

In the definitions of the groups in Formula (I) and Formula (II), the lower alkyl and the lower alkyl moiety of the mono- or di-(lower alkyl) amino, mono- or di-(lower alkyl) aminocarbonyl, lower alkanoylamino, lower alkoxy, lower alkylthio, lower alkoxycarbonyl, lower alkanoyl, and lower alkanoyloxy mean a straight-chain or branched alkyl group having 1 to 8 carbon atoms, such as methyl, ethyl, propyl, isopropyl, butyl, isobutyl, sec-butyl, tert-butyl, pentyl, isopentyl, hexyl, heptyl, and octyl. The alkenyl means a straight-chain or branched alkenyl group having 2 to 6 carbon atoms, such as vinyl, allyl, methacryl, crotyl, 3-butenyl, 2-pentenyl, 4-pentenyl, 2-hexenyl, and 5-hexenyl. The cycloalkyl means a straight-chain or branched cycloalkyl group having 3 to 8 carbon atoms, such as cyclopropyl, cyclobutyl, cyclopentyl, cyclohexyl, cycloheptyl and cyclooctyl. The aryl includes phenyl or naphthyl, and the aralkyl and the aralkyl moiety of the aralkyloxy mean an aralkyl group having 7 to 13 carbon atoms, such as benzyl, phenethyl, benzhydryl and naphthylmethyl. The heterocyclic group includes pyrrolidinyl, piperidino, piperazinyl, morpholino, thiomorpholino, homopiperazinyl, pyridyl, pyrazolyl, quinolyl, and quinazolyl. The halogen includes fluorine, chlorine, bromine and iodine atoms.

The substituted lower alkyl and the substituted lower alkoxy each has 1 to 3 independently selected substituents. Examples of the substituents are halogen, nitro, cyano, hydroxy, lower alkoxy, carboxy, lower alkoxycarbonyl, lower alkanoyl, cycloalkyl, amino, mono- or di(lower alkyl) amino, and phthalimide. The substituted aryl and substituted aralkyl each has 1 to 3 independently selected substituents on the benzene ring thereof. Examples of the substituents are halogen, lower alkyl, nitro, cyano, amino, mono- or di(lower alkyl)amino, hydroxy, lower alkoxy, carboxy, lower alkoxycarbonyl, lower alkanoyl, methylene dioxy, and trifluoromethyl. The substituted heterocyclic group has 1 to 3 independently selected substituents. Example of the substituents are halogen, lower alkyl, amino, mono- or di(lower alkyl)amino, hydroxy, lower alkoxy, carboxy, lower alkoxycarbonyl, lower alkanoyl, trifluoromethyl, phenyl and aralkyl.

In the definitions of the substituents, the halogen, the lower alkoxy, the lower alkoxycarbonyl, the lower alkanoyl, the cycloalkyl, the mono- or di(lower alkyl)amino, the lower alkyl and the aralkyl have the same meanings as defined above.

The pharmaceutically acceptable salts of the adenosine uptake inhibitor to be used in accordance with the present invention includes pharmaceutically acceptable acid addition salts, metal salts, ammonium salts, organic amine addition salts and amino acid addition salts.

Examples of the pharmaceutically acceptable acid addition salts of the adenosine uptake inhibitor include are inorganic acid addition salts such as hydrochloride salt, sulfate salt, and phosphate salt; and organic acid addition salts such as acetate salt, maleate salt, fumarate salt, tartrate salt, citrate salt and methanesulfonate salt. Examples of the pharmaceutically acceptable metal salts are alkali metal salts such as sodium salt and potassium salt; alkali earth metal salts such as magnesium salt and calcium salt; aluminium salt; zinc salt. Examples of the pharmaceutically acceptable ammonium salts are ammonium salt and tetramethylammonium salt. Examples of the pharmaceutically acceptable organic amine addition salts are addition salts with morpholine and piperidine. Examples of the pharmaceutically acceptable amino acid addition salts are addition salts with lysine, glycine, and phenylalanine.

The adenosine uptake inhibitor to be used in accordance with the present invention can be produced by the methods disclosed in the publications or according to the methods. The intermediates and desired compounds in the processes can be isolated and purified by purification methods conventionally used in organic synthetic chemistry, for example, neutralization, filtration, extraction, rinsing, drying, concentration, recrystallization, and various kind of chromatography.

In the case where a salt of the adenosine uptake inhibitor is desired and it is produced in the form of the desired salt, it can be subjected to purification as such. In the case where the adenosine uptake inhibitor is produced in the free state and its salt desired, the adenosine uptake inhibitor is dissolved or suspended in a suitable organic solvent, followed by addition of an acid or a base to form a salt.

The adenosine uptake inhibitor and pharmaceutically acceptable salts thereof may be in the form of adducts with water or various solvents, which may satisfactorily be used as the therapeutic agent of the present invention.

Some of the adenosine uptake inhibitor to be used in accordance with the present invention have optical isomers, and all potential stereoisomers and mixtures thereof may satisfactorily be used as the therapeutic agent of the present invention.

Specific examples of the adenosine uptake inhibitor to be used in accordance with the present invention are shown in Table 1.

TABLE 1

| Compound No. | |
|---|---|
| 1 |  |
| 2 |  |
| 3 |  |

TABLE 1-continued

Compound No.

4

COMPOUND 1
3-[1-(6,7-Diethoxy-2-morpholino-4-quinazolynyl)-4-piperidinyl]-1,2,3,4-tetrahydro-1,6-dimethyl-2,4-dioxoquinazoline hydrochloride salt (WO 96/06841)

Melting point: 193°–195° C.

$^1$H-NMR(CDCl$_3$)δ: 8.49(br-s, 1H), 8.00(s, 1H), 7.50(d, 1H, J=8.5Hz), 7.11(d, 1H, J=8.5Hz), 7.07(s, 1H), 5.45–5.30 (m, 1H), 4.66–4.61(br.-d, 2H), 4.35–4.32(m, 2H), 4.13–4.08 (m, 6H), 3.84(br.-s, 4H), 3.57(s, 3H), 3.40–3.31(br.-t, 2H), 3.01–2.89(m, 2H), 2.43(s, 3H), 1.92–1.88(br.-d, 2H), 1.50(t, 3H, J=7.0Hz), 1.48(t, 3H, J=7.0Hz).

COMPOUND 2
2-Aminocarbonyl-N-(4-amino-2,6-dichlorophenyl)-4-[5,5-bis(4-fluorophenyl)pentyl]-1-piperazine acetamide (Japanese Published Unexamined Patent Application No. 290869/88)

Melting point: 118°–120° C.

Value of elemental analysis: C$_{30}$H$_{33}$Cl$_2$F$_2$N$_5$O$_2$
Calculated value (%): C 59.61, H 5.50, N 11.58
Experimental value (%) C 59.53, H 5.45, N 11.58
IR(KBr) ν max (cm$^{-1}$) 1668, 1601, 1506, 1223, 1157.
$^1$H-NMR(CDCl$_3$) δ: 7.19–7.14(m, 4H), 7.00–6.93(m, 4H), 6.67(s, 2H), 4.31(s, 2H), 3.89–3.83(br-t, 1H), 3.39–3.07(m, 4H), 2.86–2.82(br-d, 1H), 2.50–2.44(m, 2H), 2.35–2.29(br-t, 2H), 2.04–1.95(m, 2H), 1.58–1.47(m, 2H), 1.30–1.22(m, 2H).

COMPOUND 3
2-Aminocarbonyl-N-(2,6-dichloro-4-nitrophenyl)-4-[(4,5-diphenyl-2-oxazolyl)methyl]-1-piperazine acetamide . dihydrochloride salt (Japanese Published Unexamined Patent Application No. 157472/94)

Melting point: 183°–185° C.

Value of elemental analysis: C$_{29}$H$_{26}$Cl$_2$N$_6$O$_5$ 2HCl
Calculated value (%): C 51.04, H 4.14, N 12.32
Experimental value (%): C 51.35, H 4.26, N 12.14
IR(KBr) ν max (cm$^{-1}$): 1687, 1514, 1446, 1389, 1346.
1H-NMR(CDCl$_3$) δ: 8.26(s, 2H), 7.64–7.55(m, 4H), 7.42–7.32(m, 6H), 3.94–3.67(m, 3H), 3.48–3.33(m, 2H), 3.20–3.05(m, 2H), 2.96–2.76(m, 4H).

COMPOUND 4
3-[1-[6-ethoxy-7-(2-hidroxyethyl)oxy-2-morpholino-4-quinazolynyl]-4-piperidinyl]-1,2,3,4-tetrahydro-1,6-dimethyl-2,4-dioxoquinazoline(WO97/29749)

Melting point: 236°–237° C.

IR(KBr tab.) (cm$^{-1}$): 1701, 1655, 1560, 1483, 1439, 1238.
$^1$H-NMR(CDCl$_3$) δ: 8.01(d, 1H, J=2.0Hz), 7.49(dd, 1H, J=8.3, 2.0Hz), 7.11(s, 1H), 7.09(d; 1H, J=8.3Hz), 6.96(s, 1H), 5.28–5.21(m, 1H), 4.27–4.20(m, 4H), 4.12(q, 2H, J=7.0Hz), 4.05–4.02(m, 2H), 3.84–3.79(m, 8H),3.58(s, 3H), 3.15–2.96(m, 4H), 2.42(s, 3H), 1.82–1.78(br.-d, 2H), 1.49(t, 3H, J=7.0Hz).

Then, the pharmacological actions of the Compounds (I) and Compound (II) are described in test examples.

TEST EXAMPLE 1
Test of the effects on murine cerulein pancreatitis

Experiment was conducted in accordance with the method described in Digestive Diseases and Science, 37, 274–279 (1992). Female BALB/C mice weighing 17 to 24 g were fasted for 16 hours. Water was provided ad libitum. Acute pancreatitis was induced by the administration of seven intraperitoueally injections of cerulein (50 μg/kg) at hourly intervals. Blood was drawn from abdominal vein, 3, 6, and 9 hours after the first injection of cerulein in case of Compound 1, Compound 2 and compound 3, while in case of Compound 4, blood was drawn therefrom 7 hours after the first injection of cerulein. Blood samples were centrifuged at 4° C. and 3,000 rpm for 10 minutes, and serum was separated. Serum amylase (Amy), lipase (Lip), and glutamic pyruvic transaminase (GPT) activities were measured. For Compound 1, Compound 2 and Compound 3, serum Amy was assayed with AU500/550 specific reagent "Katayama" Amy test(Katayama Chemical Industry Co., Ltd.); for Compound 4, serum Amy was assayed with "Rikitech P-AMY EPS" of BM pancreas-related reagent series (Boehringer Mannheim K. K.). Serum GPT was assayed with "Katayama" GPT test (Katayama Chemical Industry, Co., Ltd.). Serum Lip was assayed with an auto-analyzer reagent "Kyowa" Determiner Lipase (Kyowa Medex, Co., Ltd.). Compound 1, Compound 2, and Compound 3 were suspended in 0.5% methyl cellulose, and one orally administered hour before the first injection of cerulein, the resulting suspension was orally given at a dose of 10 ml/kg. The solvent (0.5% methyl cellulose) was similarly given to a control group. Compound 4 was dissolved in distilled water, which was adjusted to pH 2 with 0.1N HCl, and then the resulting solution was adjusted to pH 4.5 with 0.1N sodium hydroxide. Compound 4 was orally administered one hour before the first injection of cerulein. The solvent (distilled water for injections, after adjustment to pH 4.5 with 0.1N HCl) was similarly given to a control group.

Results are expressed as means±SEM where appropriate. Difference between normal group and control group were evaluated using the Wilcoxon's rank sum test. And for differences between control group and test compound-treated group, the Steel's test was used for Compound 1 and the Wilcoxon's rank sum test was used for Compounds 2, Compound 3 and Compound 4.

The effects of Compound 1, Compound 2 and Compound 3 on serum Amy, serum Lip and serum GPT are shown in Tables 2, 3 and 4; and the effect of Compound 4 are shown in Table 5.

TABLE 2

| Test groups | Dose of test compound (mg/kg) | Serum amylase (IU/L) Time after the first injection of cerulein | | |
|---|---|---|---|---|
| | | 3 | 6 | 9 |
| Normal | | 3758 ± 117 | 4067 ± 79 | 3883 ± 191 |
| Control | | 5125 ± 203** | 7817 ± 501** | 15917 ± 567** |
| Compound 1 | 10 | 4283 ± 245 | 4967 ± 167## | 14817 ± 1459 |
| Compound 1 | 30 | 4133 ± 264# | 5200 ± 274## | 5658 ± 682## |
| Normal | | 4192 ± 152 | 3650 ± 298 | 3508 ± 123 |
| Control | | 4108 ± 326 | 5908 ± 348** | 15150 ± 951** |
| Compound 2 | 300 | 4967 ± 291 | 4417 ± 305# | 9517 ± 23# |
| Compound 3 | 30 | 4050 ± 309 | 3733 ± 149## | 3958 ± 146## |

**p < 0.01 (compared with the normal group)
p < 0.05 (compared with the control group)
p < 0.01 (compared with the control group)

TABLE 3

| Test groups | Dose of test compound (mg/kg) | Serum lipase (IU/L) Time after the first injection of cerulein | | |
|---|---|---|---|---|
| | | 3 | 6 | 9 |
| Normal | | 17 ± 1 | 24 ± 2 | 24 ± 2 |
| Control | | 93 ± 13** | 190 ± 38** | 503 ± 39* |
| Compound 1 | 10 | 55 ± 3## | 91 ± 22# | 466 ± 74 |
| Compound 1 | 30 | 58 ± 5# | 81 ± 8# | 95 ± 15## |
| Normal | | 88 ± 2 | 85 ± 3 | 89 ± 4 |
| Control | | 158 ± 12** | 261 ± 22** | 730 ± 64** |
| Compound 2 | 300 | 238 ± 9## | 217 ± 51 | 726 ± 23 |
| Compound 3 | 30 | 243 ± 40# | 135 ± 6## | 200± 13## |

*p < 0.05 (compared with the normal group)
**p < 0.01 (compared with the normal group)
p < 0.05 (compared with the control group)
p < 0.01 (compared with the control group)

TABLE 4

| Test groups | Dose of test compound (mg/kg) | Serum GPT (IU/L) Time after the first injection of cerulein | | |
|---|---|---|---|---|
| | | 3 | 6 | 9 |
| Normal | | 33 ± 3 | 41 ± 5 | 50 ± 5 |
| Control | | 44 ± 2** | 80 ± 3** | 106 ± 6** |
| Compound 1 | 10 | 37 ± 3# | 50 ± 3# | 76 ± 5# |
| Compound 1 | 30 | 32 ± 3# | 51 ± 6# | 52 ± 5## |
| Normal | | 21 ± 1 | 22 ± 1 | 27 ± 1 |
| Control | | 40 ± 4** | 88 ± 7** | 141 ± 6** |
| Compound 2 | 300 | 55 ± 2## | 59 ± 6# | 129 ± 23 |
| Compound 3 | 30 | 64 ± 11# | 40 ± 1## | 59 ± 7## |

*p < 0.05 (compared with the normal group)
**p < 0.01 (compared with the normal group)
p < 0.05 (compared with the control group)
p < 0.01 (compared with the control group)

TABLE 5

| Test groups | Dose of test compound (mg/kg) | Serum Amirase (IU/l) | Serum Lipase (IU/l) | Serum GPT (IU/l) |
|---|---|---|---|---|
| | | 7 hours after the first injection of cerulein | | |
| Reference | | 99920 ± 457 | 22 ± 1 | 23 ± 2 |
| Control | | 23230 ± 2576* | 466 ± 102* | 108 ± 7* |
| Compound 4 | 10 | 14690 ± 922# | 195 ± 23# | 67 ± 2# |

*p < 0.05 (compared with reference group)
p < 0.05 (compared with control group)

The above results indicate that Compound (I) and Compound (II) or pharmacologically acceptable salts thereof have an inhibitory action on the enzymes as the markers of pancreatitis and these are therefore useful as the therapeutic agent of pancreatitis.

TEST EXAMPLE 2

Test of the effects on murine pancreatitis induced by choline—deficient and ethionine—supplemented (CDE) diet Experiment was conducted in accordance with the method described in International Journal of Pancreatology, 11, 59–65 (1992). Female CDF 1 mice weighing 15 to 21 g were fasted for 24 hours. Water provided ad libitum. Acute paucreatitis was induced in mice by means of a choline—deficient diet that was supplemented with 0.5% of DL-ethionine for 72 hours. Seventy-two hours later, the CDE diet was changed to normal diet, and the mortality was observed up to 144 hours later. The survival rate was evaluated as an indicator of the severity of pancreatitis.

Compound 1 suspended in 0.5% methyl cellulose was orally given at a dose of 1, 3 and 10 mg/kg to the mice 0, 24, 48, 72, 96 and 120 hours after the onset of CDE diet. To a control group, the solvent (0.5% methyl cellulose) was similarly given. Alternatively, dosing was initiated in a group with induced pancreatitis (therapeutic administration). Compound 1 was orally given at a dose of 10 mg/kg to this group, 32, 56, 80, 104 and 128 hours after the onset of CDE diet.

The following groups were set;
1. normal group (n=20)
2. control group (n=30)
3. group at a dose of 1 mg/kg of Compound 1 (n=30)
4. group at a dose of 3 mg/kg of Compound 1 (n=30)
5. group at a prophylactic dose of 10 mg/kg of Compound 1 (n=30)
6. group at a therapeutic dose of 10 mg/kg of Compound 1 (n=30).

The survival rate was expressed in percentage (as the percentage of the survived animals in number to the whole in logarithm); and difference was evaluated using the Fisher's exact method. Significant difference was defined at a risk factor of less than 5%.

Figure 1:
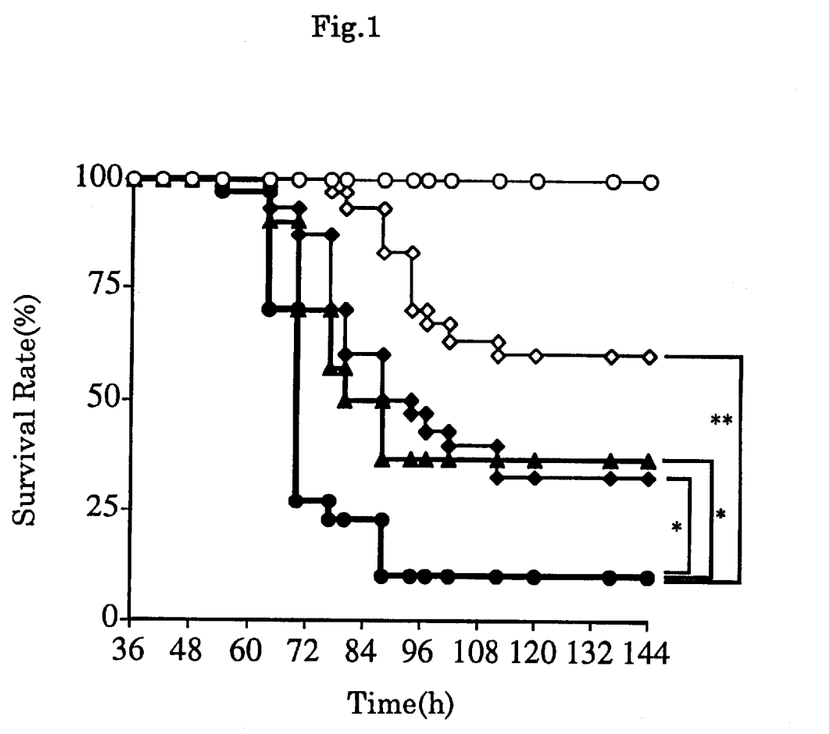
FIG. 1 is a graph showing the effects of the test compound on the murine pancreatitis induced by CDE diet.
Figure 2:
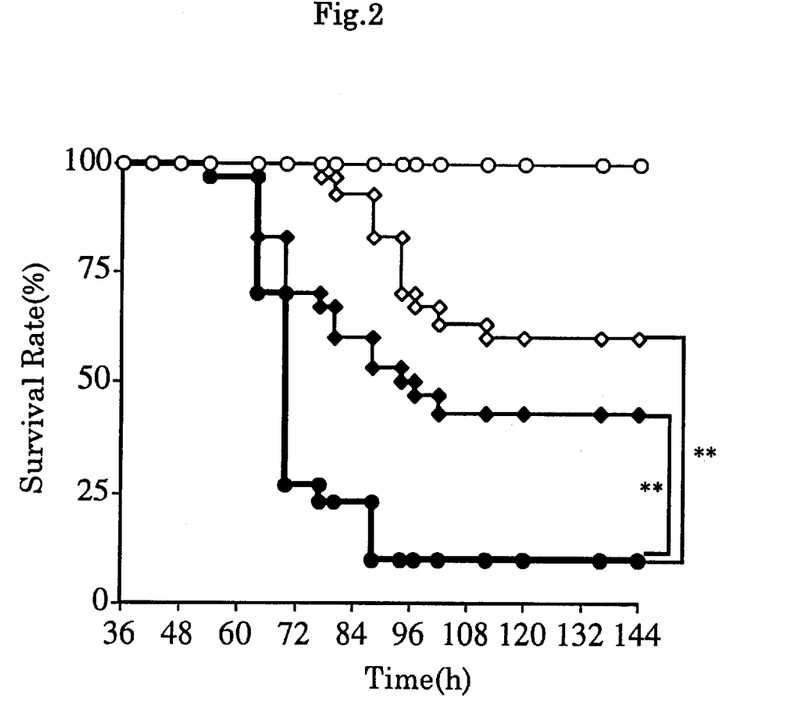
FIG. 2 is a graph showing the effects of the test compound on murine pancreatitis induced by CDE diet.

The effect of the test compound on the survival rate are shown in FIG. 1 and FIG. 2.

TEST EXAMPLE 3

Inhibitory Effect of [$^3$H]-Adenosine Uptake

A blood sample was obtained from a healthy male adult under 40 years of age by branchial venipuncture using a syringe containing sodium citrate and subjected to centrifugation to obtain washed erythrocytes. To 100 μl of an erythrocyte suspension (2.5×10$^9$ cells/ml), 10 μl of a 21% dimethylsulfoxide (DMSO) solution of a test compound was added. After allowing the suspension to stand at room temperature for 1 hour, 100 μl of a [$^3$H]-adenosine solution was added thereto. Ten seconds later, 200 μl of a dilazep solution (1 mg/ml) was added to stop the adenosine uptake. Then, dibutyl phthalate was added dropwise to the reaction mixture, followed by centrifugation. The supernatant was removed and the erythrocyte fraction was separated. The erythrocytes were dissolved in Triton X-100, and uptake amount of $^3$H was measured with a liquid scintillation counter. The concentration of the test compound which inhibits the [$^3$H]-adenosine uptake by 50% ($IC_{50}$) was calculated.

Consequently, any of the compound group described in this specification had $IC_{50}$ values of $10^{-6}$M or less.

TEST EXAMPLE 4

Acute Toxicity Test

Test compounds were orally or intraperitoneally administered to groups of dd-strain male mice weighing 20±1 g, each group consisting of three mice. Seven days after the administration, the mortality was observed to obtain a minimum lethal dose (MLD) of the compound.

Consequently, the MLD value of Compound 1 was greater than 1000 mg/kg for oral dosing; and greater than 100 mg/kg for intraperitoneal dosing. Additionally, the MLD value of Compound 2 was greater than 300 mg/kg for oral dosing; and greater than 100 mg/kg for intraperitoneal dosing.

The adenosine uptake inhibitor and pharmaceutically acceptable salts thereof to be used in accordance with the present invention can be administered as they are, or in the forms of various pharmaceutical compositions. The pharmaceutical compositions in accordance with the present invention can be prepared by uniformly mixing an effective amount of adenosine uptake inhibitor or pharmaceutically acceptable salts thereof, as an active ingredient, with a pharmacologically acceptable carrier. It is desired that such pharmaceutical compositions are prepared in a unit dose form suitable for oral or parenteral (subcutaneous, intra-rectum, intravenous or intra-muscular) administration.

For preparing a pharmaceutical composition for oral administration, any useful pharmaceutically acceptable carrier can be used. For example, liquid preparations for oral administration such as suspensions and syrups can be prepared by using water, sugars such as sucrose, sorbitol, and fructose; glycols such as polyethylene glycol and propylene glycol; oils such as sesame oil, olive oil, and soybean oil; preservatives such as p-hydroxybenzoates; flavors such as strawberry flavor and peppermint, and the like. Powders, pills, capsules and tablets can be prepared using excipients such as lactose, glucose, sucrose, and mannitol; disintegrating agents such as starch and sodium alginate; lubricants such as magnesium stearate and talc; binders such as polyvinyl alcohol, hydroxypropyl cellulose and gelatin; surfactants such as fatty acid esters; and plasticizers such as glycerin, and the like. Tablets and capsules are the most useful oral unit dose forms because of the readiness of administration. For preparing tables and capsules, solid pharmaceutical carriers are used.

Injectable preparations can be prepared using a carrier such as distilled water, a salt solution, a glucose solution, or a mixture of a salt solution and a glucose solution. The preparations can be prepared in the form of solution, suspension or dispersion according to a conventional method by using a suitable solubilizing auxiliary or suspending agent.

The adenosine uptake inhibitor and pharmaceutically acceptable salts thereof to be used in accordance with the present invention can be administered orally or parenterally in the said dosage form. The effective dose and the administration schedule vary depending upon the mode of administration, the age, body weight, and conditions of a patient, etc. However, it is generally appropriate to administer the adenosine uptake inhibitor and a pharmaceutically acceptable salt thereof in a dose of 1 to 900 mg/60 kg/day, preferably 1 to 200 mg/60 kg/day.

BRIEF DESCRIPTION OF THE DRAWINGS

—○—:normal group

—●—:control group

—▲—:group at a dose of 1 mg/kg of Compound 1

—◆—:group at a dose of 3 mg/kg of Compound 1

—◇—:group at a dose of 10 mg/kg of Compound 1

—○—:normal group

—●—:control group

—◆—:group at a prophylactic dose of 10 mg/kg of Compound 1

—◇—:group at a therapeutic dose of 10 mg/kg of Compound 1

DESCRIPTION OF THE PREFERRED EMBODIMENTS

The embodiments of the present invention will now be described in Examples.

EXAMPLE 1

Tablet

Tablets having the following composition were prepared in a conventional manner.

Compound 1 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

Composition of One Tablet

| | |
|---|---:|
| Compound 1 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 2

Capsules

Capsules having the following composition were prepared in a conventional manner.

Compound 2 (200 g) was mixed with 995 g of Avicel and 5 g of magnesium stearate. The mixture was put in hard capsules No. 4 each having a capacity of 120 g by using a

13 capsule filler (Model LZ-64, Zanasi) to give capsules each containing 20 mg of the active ingredient.
Composition of One Capsule

| Compound 2 | 20 mg |
|---|---|
| Avicel | 99.5 mg |
| Magnesium Stearate | 0.5 mg |
| | 120 mg |

EXAMPLE 3

Injections

Injections having the following composition were prepared in a conventional manner.

Compound 3 (1 g) was dissolved in 100 g of purified soybean oil, followed by addition of 12 g of purified egg yolk lecithin and 25 g of glycerin for injection. The resultant mixture was made up to 1,000 ml with distilled water for injection, thoroughly mixed, and emulsified by a conventional method. The resultant dispersion was subjected to aseptic filtration by using 0.2 μm disposable membrane filters, and then aseptically put into glass vials in 2 ml portions to give injections containing 2 mg of the active ingredient per vial.
Composition of One Injection Vial

| Compound 3 | 2 mg |
|---|---|
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

EXAMPLE 4

Anal suppository

Formulations for rectal dosing having the following composition were prepared in a conventional manner.

678.8 g of Witepzol® H15 (manufactured by Dynamite Nobel, Co.) and 290.9 g of Witepzol® E75 (manufactured by Dynamite Nobel, Co.) were melt at 40° to 50° C. Into the resulting molten matter were homogeneously mixed and dispersed 2.5 g of Compound 1, 13.6 g of potassium primary phosphate and 14.2 g of sodium secondary phosphate individually. The resultant dispersion was put in a plastic suppository mold, and then followed by gradual cooling to form into formulations containing 2.5 mg of the active ingredient per formulation.
Composition of One Formulation

| Compound 1 | 2.5 mg |
|---|---|
| Whitepzol H15 | 678.8 mg |
| Whitepzol E75 | 290.9 mg |
| potassium dihydrogen phosphate | 13.6 mg |
| disodium phosphate | 14.2 mg |
| | 1000 mg |

The present invent ion provides a prophylactic agent or a therapeutic agent of pancreatitis, containing an adenosine uptake inhibitor or pharmaceutically acceptable salts thereof as the effective ingredient.

14

What is claimed is:

1. A method for preventing or treating pancreatitis, which comprises administering a composition containing an effective amount of an adenosine uptake inhibitor or a pharmaceutically acceptable salt thereof as an active ingredient.

2. A method for preventing or treating pancreatitis according to claim 1, wherein the adenosine uptake inhibitor is a quinazoline derivative represented by the following Formula (I);

wherein $R^1$ represents hydrogen, substituted or unsubstituted lower alkyl, alkenyl, or substituted or unsubstituted aralkyl; $R^2$, $R^3$, $R^4$ and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; $R^6$, $R^7$, $R^8$ and $R^9$ independently represent hydrogen, lower alkyl, hydroxy, substituted or unsubstituted lower alkoxy or aralkyloxy, or any adjoining two of them are combined to form methylenedioxy, or ethylenedioxy; $R^{10}$ represents hydrogen, substituted or unsubstituted lower alkyl, halogen, or $NR^{12}R^{13}$ (wherein $R^{12}$ and $R^{13}$ independently represent hydrogen, substituted or unsubstituted lower alkyl, cycloalkyl, substituted or unsubstituted aryl, or substituted or unsubstituted aralkyl; or $R^{12}$ and $R^{13}$ are combined together with N to form a substituted or unsubstituted heterocyclic group); $R^{11}$ represents hydrogen, lower alkyl, or halogen; and n represents 0, 1, or 2; or a pharmaceutically acceptable salt thereof.

3. A method for preventing or treating pancreatitis according to claim 1, wherein the adenosine uptake inhibitor is a compound represented by the following Formula (II);

wherein $R^{14}$ represents hydrogen, or lower alkyl; $R^{15}$ represents hydrogen, carbamoyl, mono- or di(lower alkyl) aminocarbonyl, lower alkoxycarbonyl, or carboxy; $R^{16}$ represents hydrogen, or lower alkyl; Ar represents substituted or unsubstituted aryl, or substituted or unsubstituted heterocyclic group; m represents 1, or 2; p represents an integer of 0 to 5; Q represents substituents selected from the group consisting of (a) to (m) represented by the following formulas;

-continued

(c)

(d)

(e)

(f)

(g)

(h)

-continued (i)

(j)

(k)

(l)

(m)

wherein Y represents S, O, or NH; $Ar^1$ and $Ar^2$ independently represent substituted or unsubstituted aryl, or substituted or unsubstituted heterocyclic group; or a pharmacologically acceptable salt thereof.

* * * * *

UNITED STATES PATENT AND TRADEMARK OFFICE
CERTIFICATE OF CORRECTION

PATENT NO. : 5,866,574

DATED : February 2, 1999

INVENTOR(S) : YUKO OKAMURA ET AL.

It is certified that error appears in the above-identified patent and that said Letters Patent is hereby corrected as shown below:

COLUMN 1

Line 37, "effect" should read --effects--.
Line 38, "which" should read --which is--.
Line 40, "increase" should read --increases--.

COLUMN 2

Line 43, "$(CH_2))_n$" should read --$(CH_2)_n$--.

COLUMN 4

Line 14, "is" should read --are--, and
  "(II),hereinafter." should read
  --(II), hereinafter.--.
Line 62, "includes" should read --include--.
Line 66, "are" should be deleted.

COLUMN 5

Line 19, "kind" should read --kinds--.

UNITED STATES PATENT AND TRADEMARK OFFICE
CERTIFICATE OF CORRECTION

PATENT NO. : 5,866,574

DATED : February 2, 1999

INVENTOR(S) : YUKO OKAMURA ET AL.

It is certified that error appears in the above-identified patent and that said Letters Patent is hereby corrected as shown below:

<u>COLUMN 7</u>

Line 42, "$(cm^1)$" should read --$(cm^1)$:--.

<u>COLUMN 8</u>

Line 23, "709(d;" should read --709(d,--.
Line 41, "compound" should read --Compound--.

<u>COLUMN 9</u>

Line 2, "Difference" should read --Differences--.
Line 10, "effect" should read --effects--.

<u>COLUMN 10</u>

Line 5, "Dose of test (IU/l) (IU/l) (IU/l)"
   should read --Dose of test (IU/L) (IU/L) (IU/l) --.
Line 57, "effect" should read --effects--.

UNITED STATES PATENT AND TRADEMARK OFFICE
CERTIFICATE OF CORRECTION

PATENT NO.  : 5,866,574

DATED       : February 2, 1999

INVENTOR(S) : YUKO OKAMURA ET AL.

It is certified that error appears in the above-identified patent and that said Letters Patent is hereby corrected as shown below:

<u>COLUMN 14</u>

Line 55, "alkyl)" should read --alkyl)- --.

Signed and Sealed this

Seventh Day of March, 2000

Attest:

Q. TODD DICKINSON

*Attesting Officer*    *Commissioner of Patents and Trademarks*